(12) United States Patent
Shen et al.

(10) Patent No.: US 9,417,209 B2
(45) Date of Patent: Aug. 16, 2016

(54) BIOSENSING WELL ARRAY WITH PROTECTIVE LAYER

(71) Applicant: Taiwan Semiconductor Manufacturing Company, Ltd., Hsin-Chu (TW)

(72) Inventors: Wei-Cheng Shen, Tainan (TW); Yi-Hsien Chang, Shetou Township (TW); Shih-Wei Lin, Taipei (TW); Chun-Ren Cheng, Hsin-Chu (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 6 days.

(21) Appl. No.: 14/703,724

(22) Filed: May 4, 2015

(65) Prior Publication Data

US 2015/0233864 A1     Aug. 20, 2015

Related U.S. Application Data

(62) Division of application No. 14/033,089, filed on Sep. 20, 2013, now Pat. No. 9,023,674.

(51) Int. Cl.
  *G01N 27/403*    (2006.01)
  *G01N 27/414*    (2006.01)

(52) U.S. Cl.
  CPC ........ *G01N 27/4145* (2013.01); *G01N 27/4148* (2013.01)

(58) Field of Classification Search
  CPC .................. G01N 27/4145; G01N 27/4148
  USPC ................................ 438/49; 257/253, 414
  See application file for complete search history.

(56) References Cited

U.S. PATENT DOCUMENTS

| | | | |
|---|---|---|---|
| 7,550,310 B2* | 6/2009 | Goodman et al. | 438/49 |
| 7,888,708 B2* | 2/2011 | Yazawa et al. | 257/253 |
| 2008/0311740 A1* | 12/2008 | Itou | 438/653 |
| 2012/0045368 A1* | 2/2012 | Hinz et al. | 422/69 |
| 2012/0223370 A1 | 9/2012 | Zan et al. | |
| 2013/0341734 A1 | 12/2013 | Merz | |
| 2014/0225166 A1* | 8/2014 | Ellis-Monaghan et al. | 257/253 |
| 2014/0264472 A1 | 9/2014 | Fife et al. | |
| 2014/0273324 A1* | 9/2014 | Fife | G01N 27/4145 438/49 |

* cited by examiner

*Primary Examiner* — Kimberly Rizkallah
*Assistant Examiner* — Maria Ligai
(74) *Attorney, Agent, or Firm* — Slater Matsil, LLP

(57) ABSTRACT

The present disclosure provides a biological field effect transistor (BioFET) and a method of fabricating a BioFET device. The method includes forming a BioFET using one or more process steps compatible with or typical to a complementary metal-oxide-semiconductor (CMOS) process. The BioFET includes a microwells having a sensing layer, a top metal stack under the sensing layer, and a multi-layer interconnect (MLI) under the top metal stack. The top metal stack includes a top metal and a protective layer over and peripherally surrounding the top metal.

22 Claims, 13 Drawing Sheets

BIOSENSING WELL ARRAY WITH PROTECTIVE LAYER

PRIORITY CLAIM

This application claims the benefit to and is a divisional of U.S. patent application Ser. No. 14/033,089, filed on Sep. 20, 2014 and entitled "BIOSENSING WELL ARRAY WITH PROTECTIVE LAYER" which application is incorporated herein by reference.

TECHNICAL FIELD

This disclosure relates to biosensors and methods for forming biosensors. Particularly, this disclosure relates to biological field-effect-transistors (bioFETs) and methods for forming them.

BACKGROUND

Biosensors are devices for sensing and detecting biomolecules and operate on the basis of electronic, electrochemical, optical, and mechanical detection principles. Biosensors that include transistors are sensors that electrically sense charges, photons, and mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert electric signals, and can be easily applied to integrated circuits (ICs) and microelectromechanical systems (MEMS).

Biochips are essentially miniaturized laboratories that can perform hundreds or thousands of simultaneous biochemical reactions. Biochips can detect particular biomolecules, measure their properties, process the signal, and may even analyze the data directly. Biochips enable researchers to quickly screen large numbers of biological analytes in small quantities for a variety of purposes, from disease diagnosis to detection of bioterrorism agents. Advanced biochips use a number of biosensors along with microfluidics to integrate reaction, sensing and sample management. BioFETs (biological field-effect transistors, or bio-organic field-effect transistors) are a type of biosensor that includes a transistor for electrically sensing biomolecules or bio-entities. While BioFETs are advantageous in many respects, challenges in their fabrication and/or operation arise, for example, due to compatibility issues between the semiconductor fabrication processes, the biological applications, restrictions and/or limits on the semiconductor fabrication processes, sensitivity and resolution of the electrical signals and biological applications, and/or other challenges arising from implementing a large scale integration (LSI) process.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
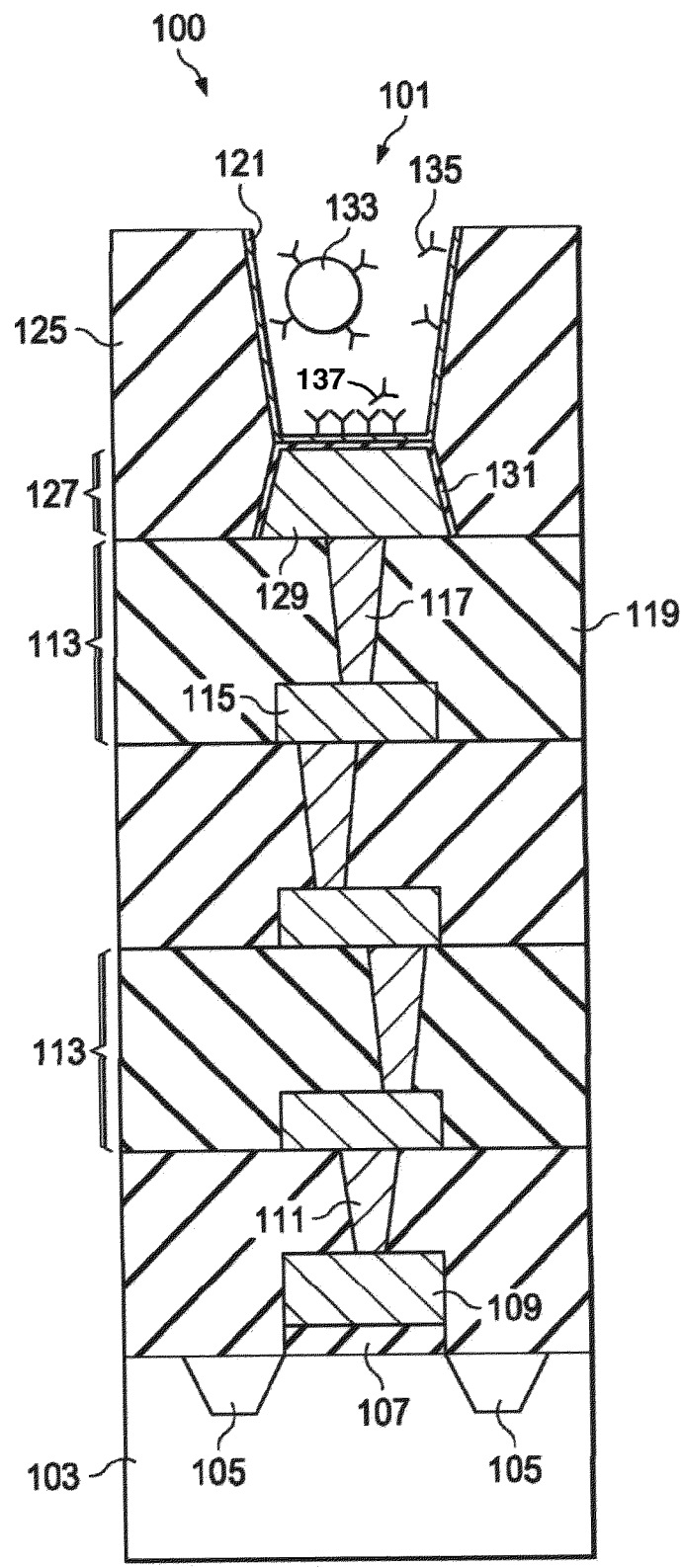
FIG. 1 is a cross-sectional view of a BioFET according to one or more embodiments in accordance with the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Further still, references to relative terms such as "top", "front", "bottom", and "back" are used to provide a relative relationship between elements and are not intended to imply any absolute direction. Various features may be arbitrarily drawn in different scales for simplicity and clarity.

In a biological field-effect transistor (BioFET), the gate of a metal-oxide-semiconductor field-effect transistor (MOSFET), which controls the conductance of the semiconductor between its source and drain contacts, includes a bio- or biochemical-compatible layer or a biofunctionalized layer of immobilized probe molecules that act as surface receptors. Essentially, a BioFET is a field-effect biosensor with a semiconductor transducer. An advantage of BioFETs is label-free operation. Specifically, using BioFETs can avoid costly and time-consuming labeling operations such as the labeling of an analyte with, for instance, fluorescent or radioactive probes.

Binding of a target biomolecule or bio-entity to the gate or a receptor molecule immobilized on the gate of the BioFET modulates the conductance of the BioFET. When the target biomolecule or bio-entity is bonded to the gate or the immobilized receptor connected to the gate, the drain current of the BioFET is varied by the gate potential, which depends on the type and amount of target bound. This change in the drain current can be measured and used to determine the type and amount of the bonding between the receptor and the target biomolecule or the biomolecule itself. In some embodiments of different circuit design, the device could work in linear or saturation region of the IV curve for biosensing. A variety of receptors may be used to functionalize the gate of the BioFET such as ions, enzymes, antibodies, ligands, receptors, peptides, oligonucleotides, cells of organs, organisms and pieces of tissue. For instance, to detect ssDNA (single-stranded deoxyribonucleic acid), the gate of the BioFET may be functionalized with immobilized complementary ssDNA strands. Also, to detect various proteins such as tumor markers, the gate of the BioFET may be functionalized with monoclonal antibodies.

One example of a biosensor has a sensing surface over a top metal plate connected to the gate of the BioFET. The metal plate and the sensing surface is a floating gate for the BioFET. The floating gate is connected to the gate structure of the BioFET through several layers of metal interconnect lines and vias (or multi-layer interconnect, MLI). In such a BioFET, the potential-modulating reaction takes place at an outer surface of the metal plate or a dielectric surface formed on top of the metal plate. Each microwell, through different sensing layers and metal plates, is connected to a different transistor. The microwell is formed over the top metal plate for each BioFET. The microwells are isolated from each other, and the reactions take place on the sensing layer in each microwell. The various microwells are connected by microfluidic channels. Reagents are flowed through the microfluidic channels to each sensing layer in the microwells. The reagents include test samples that directly bind to the sensing layer or indirectly through a carrier. An example of a carrier is a bead having the test samples bound thereon. In one example, the binding reaction changes a local ion concentration (pH) in a microwell that causes a change in the internal charge of the sensing layer. The charge of the sensing layer is transmitted to the transistor gate through the various metal layers as a voltage signal. The change in gate voltage changes the amount of current flowing between the source and drain of the BioFET. By detecting the current, the change in pH in the microwell is measured. Size of the microwells is directly related to the signal intensity. Larger microwells allow a larger sensing layer/more bio-entities that can include more binding sites to create a stronger signal.

The top metal plate is prone to corrosion if exposed to the analyte; such corrosion would render the BioFET defective. While the sensing layer protects the top metal plate from the analyte, a bottom of the microwell is sized to be smaller than the top surface of the top metal plate within alignment tolerances to further ensure that the top metal plate is not exposed to the analyte. In other words, the bottom of the microwell is sufficiently small such that even with misalignment, the microwell would still be situated over the metal plate. Adequate spacing is maintained between adjacent top metal plates to isolate the microwells from each other as well as following the design rules for the top metal electrodes.

An increase in biochip capacity is desirable to allow more simultaneous reactions and more accurate measurements. Higher biochip capacity involves building more transistors and a higher number of corresponding microwells. Having more microwells reduces the area of each microwell, as only a finite space is available on the biochip. When the size of the microwells decreases, the area of the sensing layer also decreases, which decreases signal intensity and increases signal-to-noise ratio (SNR).

One way to minimize the decrease in signal intensity involves preserving the sensing layer area as the number of microwells increase. In some examples, microwells having bottoms larger than the top metal plate are used. The larger microwell bottom increases the sensing layer area. While the microwells are larger, a gap between the top metal plate and the passivation wall may be created that are filled by the sensing layer. A misalignment between the microwell and the top metal plate can create a crack corrosion site and render the transistor defective. With metal sensing layers, the likelihood that the sensing layer bridges to the top metal of an adjacent microwell increases when there is a misalignment. Therefore, having microwells with bottoms larger than the top metal makes misalignment window very small for the microwell and top metal electrode.

Other examples to increase the sensing layer area involve adding a smaller metal plug over the top metal electrode and a sensing plate over the smaller metal plug. The sensing plates may be placed closer than the top metal plates and thereby increase the area of the microwells. Having a sensing plate over the smaller metal plug reduces the likelihood of bridging signals between adjacent microwells. However, adding a smaller metal plug and a sensing plate having different dimensions adds two additional layers with two photomask patterns that increase the manufacturing cost significantly.

The present disclosure pertains to a method and structure for forming microwells that are larger as compared to the microwells over the top metal plates without misalignment issues. According to various embodiments, a top metal stack includes a protective layer over and peripherally surrounding the top metal to ensure separation of the analyte and the top metal material. A sensing layer is deposited in the microwells and over the field. At least the field portion of the sensing layer is removed in an etch process while a photomask protects the portions of the sensing layer within the microwells. The removal of the field portion of the sensing layer isolates the microwells from each other.

FIG. 1 is a cross-sectional view of a BioFET 100 according to one or more embodiments in accordance with the present disclosure. The BioFET 100 includes a substrate 103 on and in which a transistor is formed. The source and drain regions 105 are formed in the substrate 103. A gate stack including gate dielectric 107 and gate electrode 109 is formed on the substrate 103. As shown in FIG. 1, the transistor in BioFET 100 is a planar transistor; however, other types of transistors may be used, including a multi-gate transistor or a FinFET. The BioFET 100 also includes a gate contact 111 over the gate electrode 109. Contacts to the source and the drain (not shown) are also included. A number of metal interconnect layers 113 interpose between the gate contact 111 and a microwell 101. Each metal interconnect layer 113 includes a metal line 115 and metal via 117 within a layer of intermetal dielectric 119. Three metal interconnect layers 113 are shown, but fewer or more may be used.

The microwell 101 is an opening in the passivation layer 125 and includes a sensing layer 121 on the bottom and at least a portion of the sidewalls. Having sensing layer 121 on the sidewalls increases the surface area of the sensing layer 121. According to various embodiments, the sidewalls may not be fully covered by the sensing layer 121. The sensing layer 121 may be a metal, dielectric, or a polymer. Examples include titanium nitride, high-k dielectric such as aluminum oxide, lanthanum oxide, hafnium oxide, and tantalum oxide.

A top metal stack 127 is disposed between the last top metal interconnect layer 113 and microwell 101. The top metal stack 127 directly contacts the sensing layer 121 of the microwell 101 and the metal via 117 of the last top metal interconnect layer 113. The top metal stack 127 includes a top metal 129 and a protective layer 131 over and peripherally surrounding the top metal 129. The top metal stack 127 may also include an adhesion layer under the top metal 129 and an antireflection layer between the protective layer 131 and the top metal 129.

A BioFET device includes a number of BioFETs 100 with microwells 101 that are in fluidic communication with each other. Each microwell 101 is associated with gates of one or more transistors. When a microwell 101 is connected to the gates of more than one transistor, a higher frequency sampling may be performed to increase the accuracy of the measurement. The microwells are connected by microfluidic channels forming an array of BioFETs 100. The microfluidic channels allow an analyte to flow from an inlet of the BioFET device to an outlet of the BioFET device. The microfluidic channels may be above the microwells 101 as shown in FIG. 1 or be at a same level as the microwells 101. The analyte includes test samples and a carrier medium. In some embodiments, the test samples include functionalized beads 133 on which specific biomolecules 135 from the test samples would bind. The functionalized beads are sized such that only a particular numbers of them would fit in a microwell. For example, the functionalized beads 133 may be slightly smaller than a microwell such that only one bead 133 can fit in a microwell. The biomolecules 135 on the functionalized bead 133 would change the fluidic environment in the microwell 101 in a way that is detectible by the transistor. In other embodiments, the test sample includes biomolecules 137 that would bind to receptors labeled on the sensing layer 121 without using carrier beads. For example, single stranded deoxyribonucleic acid (ssDNA) is bound on the sensing layer and amplified with PCR (polymarse chain reaction) to duplicate the same DNA to increase sites. Then, reagent is flowed through the microwells for DNA sequencing. Other examples include protein labeling and anti-body/anti-gen reactions.

Figure 2A:
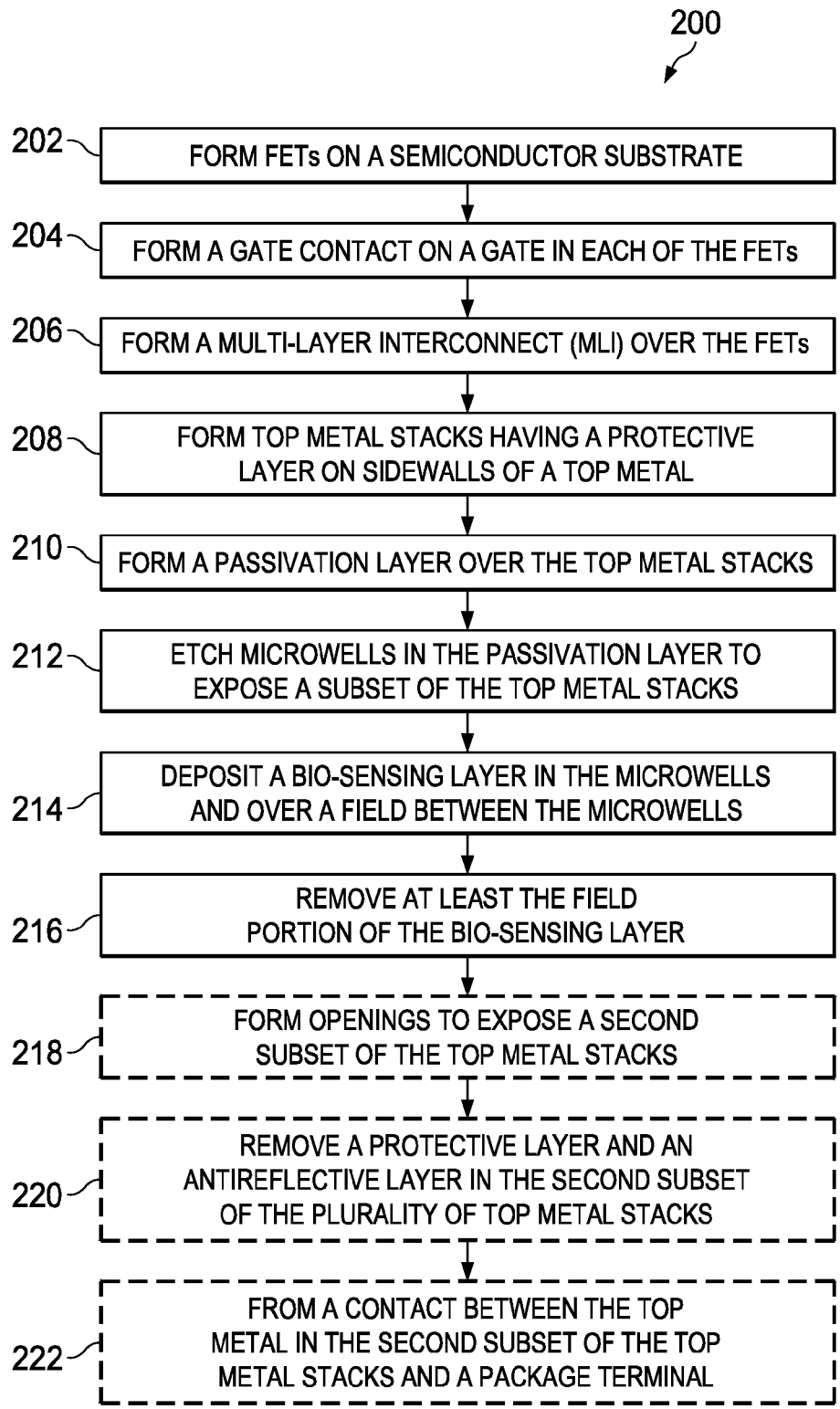
FIGS. 2A and 2B are flow charts of method embodiments of fabricating a BioFET device according to one or more aspects of the present disclosure.

FIG. 2A is a method 200 of fabricating a BioFET device according to one or more aspects of the present disclosure. The method 200 begins at operation 202 where a number of field-effect transistors (FETs) are formed on a semiconductor substrate. The semiconductor substrate may be a silicon substrate. Alternatively, the substrate may include another elementary semiconductor, such as germanium; a compound semiconductor including silicon carbide, gallium arsenic, gallium phosphide, indium phosphide, indium arsenide, and/or indium antimonide; an alloy semiconductor including SiGe, GaAsP, AlInAs, AlGaAs, GaInAs, GaInP, and/or GaInAsP; or combinations thereof. In an embodiment, the substrate is a semiconductor on insulator (SOI) substrate. The SOI substrate may include a buried oxide (BOX) layer formed by a process such as separation by implanted oxygen (SIMOX), and/or other suitable processes. The substrate may include doped regions, such as p-wells and n-wells. In the present disclosure, a wafer is a semiconductor substrate and various features formed in and over the semiconductor substrate. The wafer may be in various stages of fabrication and is processed using the CMOS process.

In operation 204, a gate contact is formed on a gate in each of the FETs. The gate contacts are formed in typical CMOS processing. Contacts are also formed over and physically connecting to the source/drain regions. In operation 206 a multi-layer interconnect (MLI) is formed over the FETs. The MLI structure may include conductive lines, conductive vias, and/or interposing dielectric layers (e.g., interlayer dielectric (ILD)). The MLI structure provides electrical connection to the transistor. The conductive lines in various levels may comprise copper, aluminum, tungsten, tantalum, titanium, nickel, cobalt, metal silicide, metal nitride, poly silicon, combinations thereof, and/or other materials possibly including one or more layers or linings. The linings include adhesion layer, barrier layer, etch stop layer, and anti-reflective coatings. The interposing or inter-layer dielectric layers (e.g., ILD layer(s)) may comprise silicon dioxide, fluorinated silicon glass (FSG), SILK (a product of Dow Chemical of Michigan), BLACK DIAMOND™ (a product of Applied Materials of Santa Clara, Calif.), and/or other insulating materials. The MLI may be formed by suitable processes typical in CMOS fabrication such as CVD, PVD, ALD, plating, spin-on coating, and/or other processes.

The number of metal layers in the MLI depends on routing needs for the FETs. For simple BioFET devices where little or no analysis and processing are performed on the device, fewer metal layers are used, for example, 3 metal layers. In some embodiments, the BioFET devices process or analyze the measurements, more metal layers are used, for example, four, five, or eight metal layers. The use of more metal layers allows more transistors to be used on the device that can perform complex logic operations with or without additional external input. Further, the results from the BioFETs can be used as input that triggers further device operations. In one example, the further device operation may flow the contents of a microwell toward a more sensitive BioFET or a BioFET where a chemical reaction would break up some of the biological content. With additional processing power, a lab-on-a-chip type of device is formed where the output from the device includes results of the analysis instead of only raw data. For example, the device may determine whether a blood sample contains cancer cells, quantify the cancer cells, and output a cancer type. In another example, the device may determine a genetic sequence.

Figure 2B:
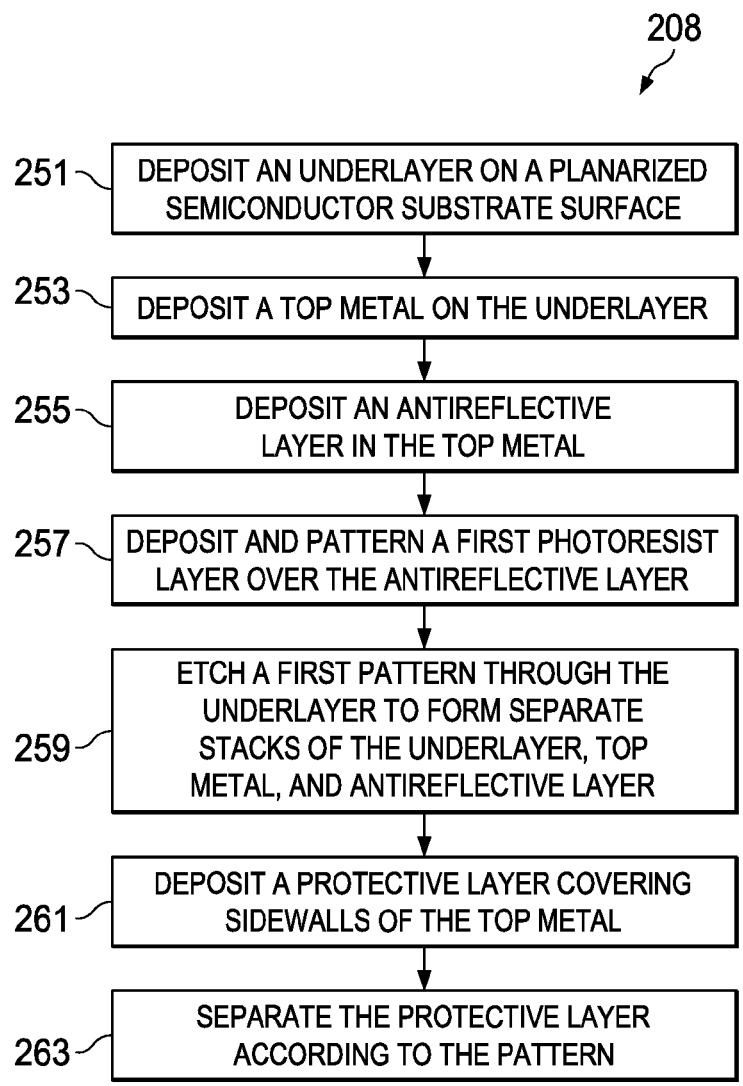

In operation 208, top metal stacks are formed. The top metal stacks have a protective layer on sidewalls of a top metal. As used herein, top metal stacks are disposed over the MLI. The top metal stacks include a number of top metals, which are metal plates. The metal plates may include aluminum, copper, or tungsten. Some metal plates are each individually connected to the gate contact of a BioFET. Other metal plates are used for signal transmission, such as bonding pads for bonding wires or bumps. FIG. 2B is a process flow diagram of the various steps of operation 208 to form the top metal stacks.

In operation 251 of FIG. 2B, an underlayer is deposited on a planarized surface over a semiconductor substrate. The planarized surface includes exposed metal vias from the MLI embedded in an intermetal dielectric (IMD). The IMD may be a silicon oxide, silicon nitride, or other commonly used IMD material including low-k dielectrics containing silicon oxide with or without pores. The underlayer may include titanium, titanium nitride, tungsten nitride, tantalum, tantalum nitride, molybdenum, titanium tungsten, or other commonly used copper diffusion barrier material. The thin underlayer acts as a barrier against copper diffusion from the underlying via to the top metal. Excessive diffusion between the copper metal layers create voids and negatively affect the conductivity of the metal layers.

In operation 253 of FIG. 2B, a top metal is deposited on the underlayer. The top metal includes copper and optionally aluminum, as a mixture or alloy. As discussed, the top metal material is prone to corrosion if exposed to analytes during the BioFET operation. The top metal is used under the microwells as well as for signal routing and external contacts.

In operation 255, an antireflective layer is deposited on the top metal. The antireflective layer (ARL) may be a titanium nitride, a silicon oxynitride, or other commonly used antireflective material. Because the top metal is highly reflective, without an ARL the top metal cannot be accurately patterned and etched using a lithography process.

Figure 3:
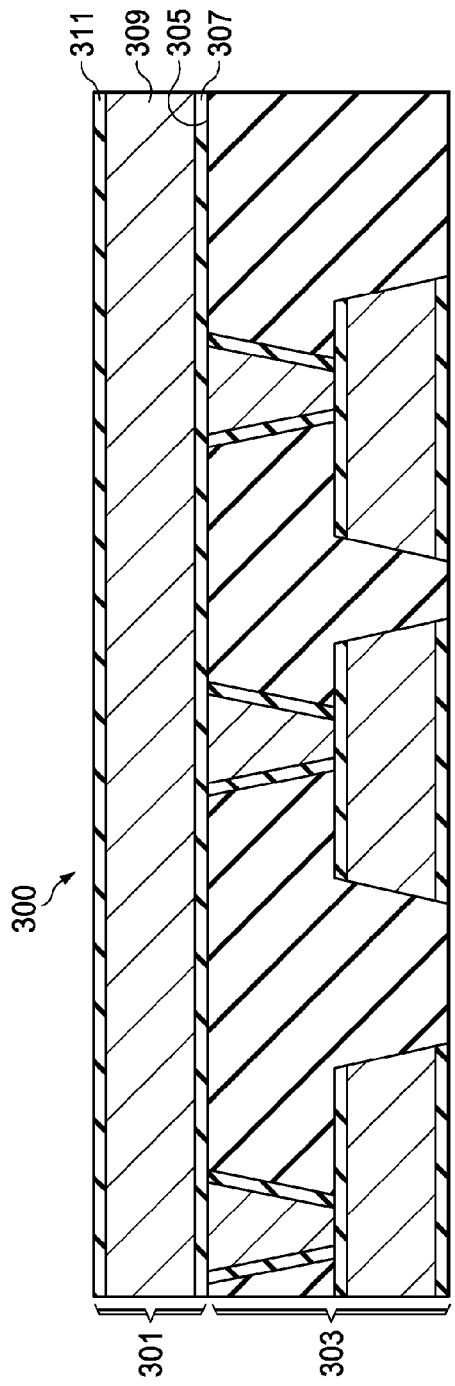
FIGS. 3 to 12 are cross-sectional views of a portion of a workpiece at various intermediate stages of forming a BioFET according to one or more aspects of the present disclosure.

FIG. 3 is a cross sectional diagram of a workpiece 300 including the top metal layers 301 deposited in operations 251, 253, and 255 over a metal layer 303 in the MLI. The top metal layers 301 are deposited on the planarized surface 305 and includes the underlayer 307, the top metal 309, and ARL 311.

Referring to FIG. 2B, in operation 257 a first photoresist is deposited and patterned over the ARL. The first photoresist is patterned to be an etch mask to etch the top metal layers. A typical lithographic process is used to deposit the photoresist, cure the photoresist, expose the photoresist to patterned light, and develop the photoresist to create a first pattern. In operation 259, the first pattern is etched through the underlayer to form separate stacks of the underlayer, top metal, and ARL. An etch process removes the ARL, the top metal, the underlayer, and a portion of the underlying IMD to separate the various top metal layers into top metal stacks. A portion of the underlying IMD is also removed to ensure complete removal of conductive material between the top metal stacks. The etch process may be a dry etch. The dry etch may use a chlorine based or a fluorine based etchant in a plasma process. In one embodiment, the etch process utilizes an end point system where the etch process detects an end point material, for example, IMD material, and signals that the end point for the etch has been reached. At the end point, the etch process continues for a defined duration to over etch an additional amount of material to ensure complete removal of conductive material between the top metal stacks.

Figure 4:
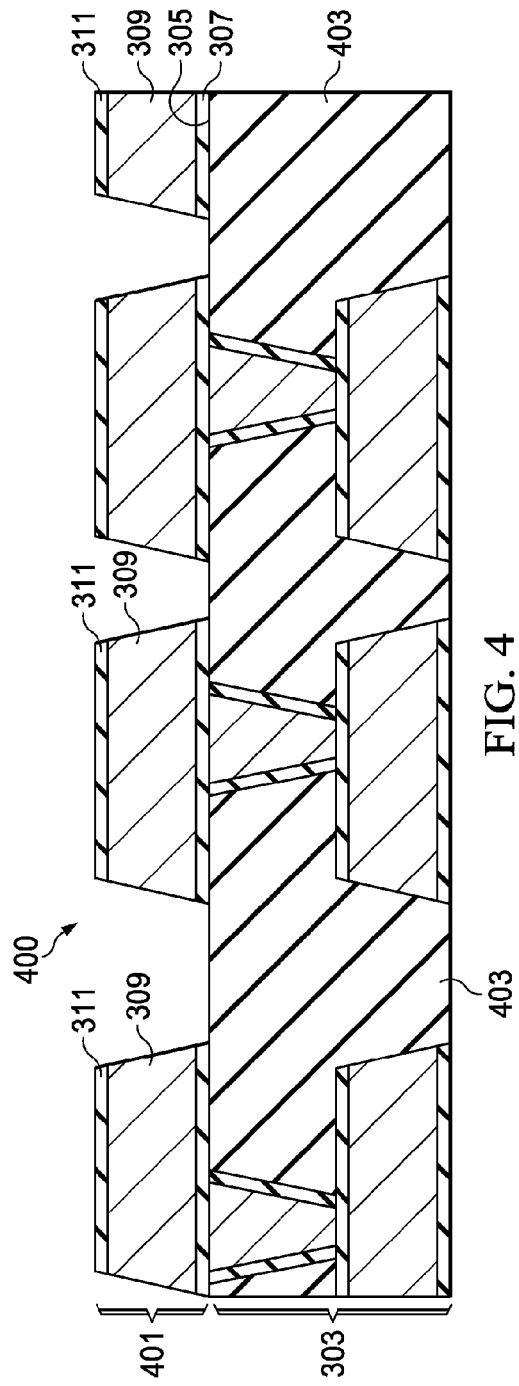

FIG. 4 is a cross sectional diagram of a workpiece 400 including four metal stacks 401 over the metal layer 303. Each metal stack 401 includes an ARL 311, a top metal 309, and an underlayer 307. As shown, a portion of the IMD 403 between the metal stacks 401 is also removed to ensure complete removal of the underlayer 307. While the top metal 309 sidewalls in FIG. 4 show a slope, according to some embodiments the etch may be performed such that the sidewalls are nearly vertical.

Figure 5:
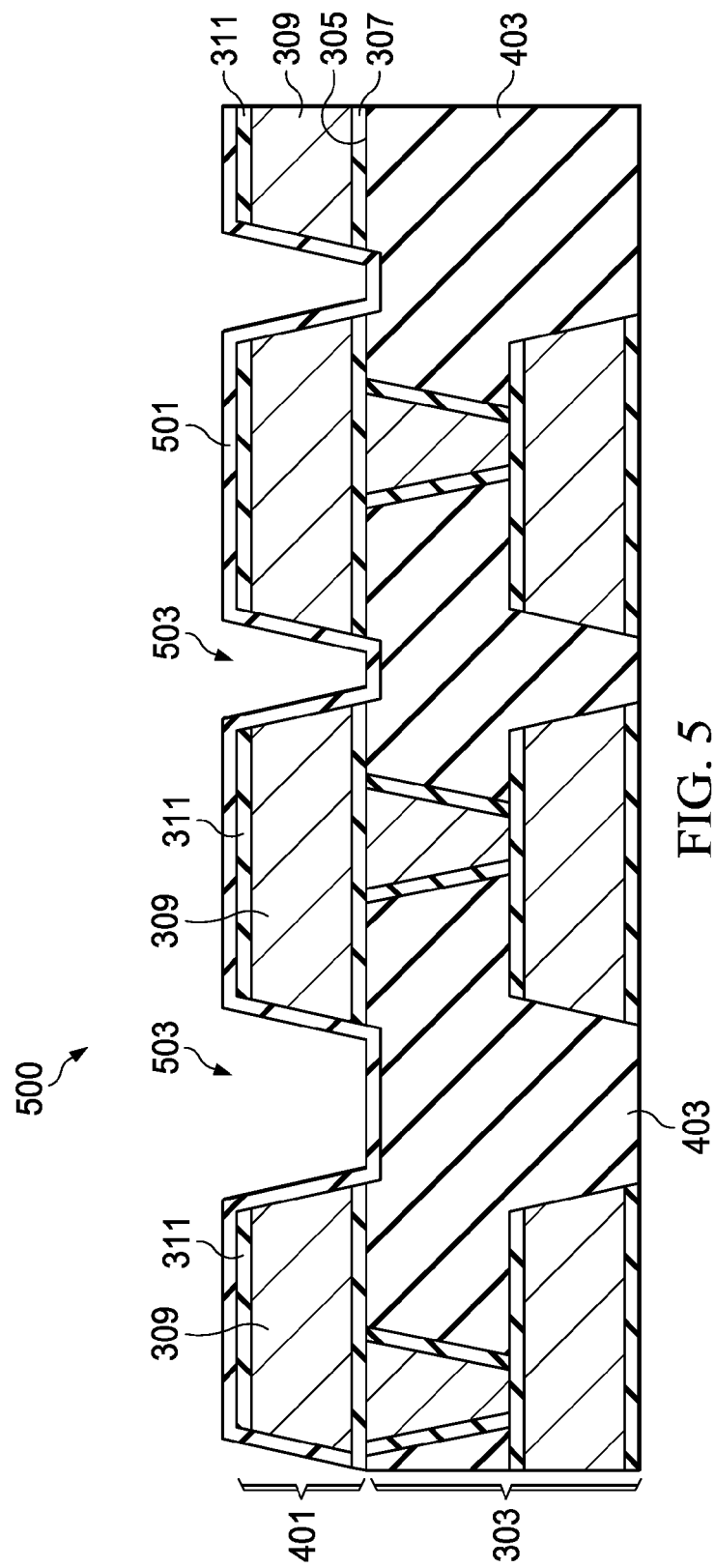

In operation 261 of FIG. 2B, a protective layer is deposited to cover top and the sidewalls of each metal stack 401. The protective layer is deposited using CVD or PVD processes and is conformal to the metal stacks formed in operation 259. The protective layer covers the sidewalls of the top metal deposited in operation 253 and patterned in operation 257. The protective layer may be a copper diffusion barrier material such as titanium, titanium nitride, tungsten nitride, tantalum, tantalum nitride, molybdenum, titanium tungsten, or other commonly used copper diffusion barrier material. Depending on the method use for deposition, a top of the metal stack may be deposited thicker than sidewalls of the metal stack. In one example, titanium nitride is deposited and has a thickness of 500 angstroms or more, for example, about 500 angstroms to about 1000 angstroms over the metal stack and a thickness of 250 angstroms or more, for example, about 300 angstroms on the sidewalls of the metal stack. The protective layer is also deposited in a bottom of the trench areas between the metal stacks. According to various embodiments, the thicknesses deposited in each area may vary depend on the aspect ratio of the trenches and the method of deposition. For example, using a PVD process, the top of metal stack and the bottom of low aspect ratios may have a thicker film than at the sidewalls. FIG. 5 is a cross sectional diagram of a workpiece 500 including four metal stacks 401 with a protective layer over all of the metal stacks and in the bottom of trenches 503.

Referring back to FIG. 2B, in operation 263 the protective layer is separated according to the pattern used to form the metal stacks in operation 259. In other words, the protective layer at the bottoms of trenches 503 is removed. In some embodiments, the protective layer is removed by dry etching without using a patterned etch mask. The dry etch process is tuned to bias an etching plasma toward horizontal surfaces of the workpiece. By directing an etching plasma downward in the trench, more material is removed from the bottom of the trench than the sidewalls. While some protective layer material would also be removed from the top of the metal stack, as long as the top metal is not exposed by the etching process, the top metal would remain protected even if the protective layer thickness over the top metal is reduced. The amount of protective layer removed from the top of the metal stack can be minimized by using an end point detection technique to detect when the IMD material underlying the protective layer is removed. As discussed, once the IMD material is detected, the etch may progress for a specified duration to ensure removal of all of the protective material from the trench bottoms. Such end point detection can also monitor whether any top material is exposed and etched by detecting the presence of copper.

Figure 6:
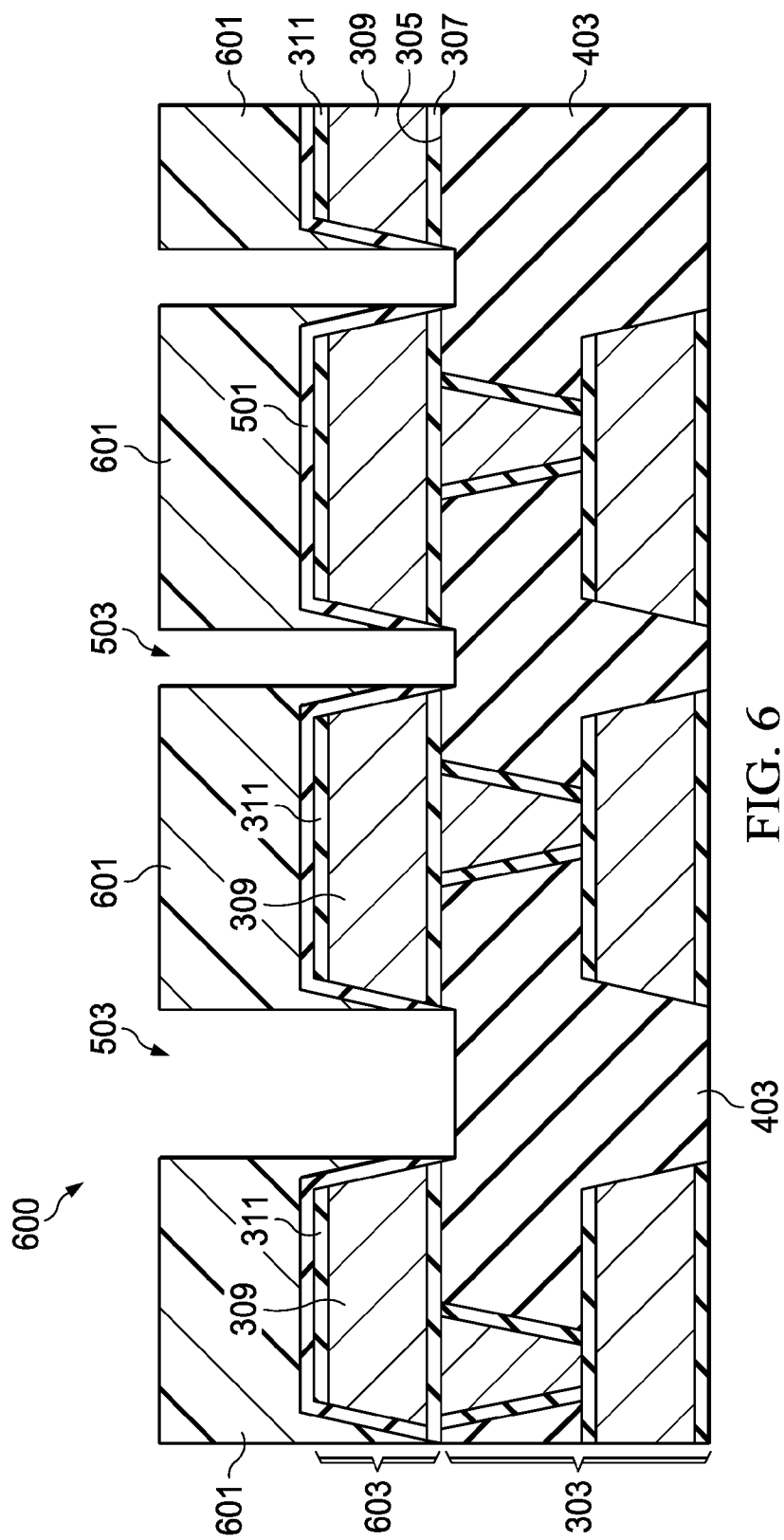

In some embodiments, the protective layer is removed by dry etching using the same photomask used in operation 257 to pattern the first photoresist. The exposure operation during the patterning may be adjusted to increase or decrease the size of the pattern developed. For example, when using a positive photoresist, a smaller intensity of light may be directed through the photomask to reduce the amount of the photoresist developed, thereby decreasing the opening such that a portion of the sidewall is protected. FIG. 6 is a cross sectional diagram of a workpiece 600 including a patterned photoresist 601 covering the sidewalls and top of the top metal stacks 603. The pattern of the photoresist 601 may be created using the same photomask using in operation 257 by changing the light intensity or other parameters. In certain embodiments, a different photomask may be used. The photoresist 601 is an etch mask protecting the top portions and sidewalls of the top metal stack 603. The protective layer 501 on the bottom of trenches 503 are removed by dry etch or wet etch. After the protective layer 501 is separated according to the pattern, the photoresist is removed, as shown in FIG. 7.

Figure 7:
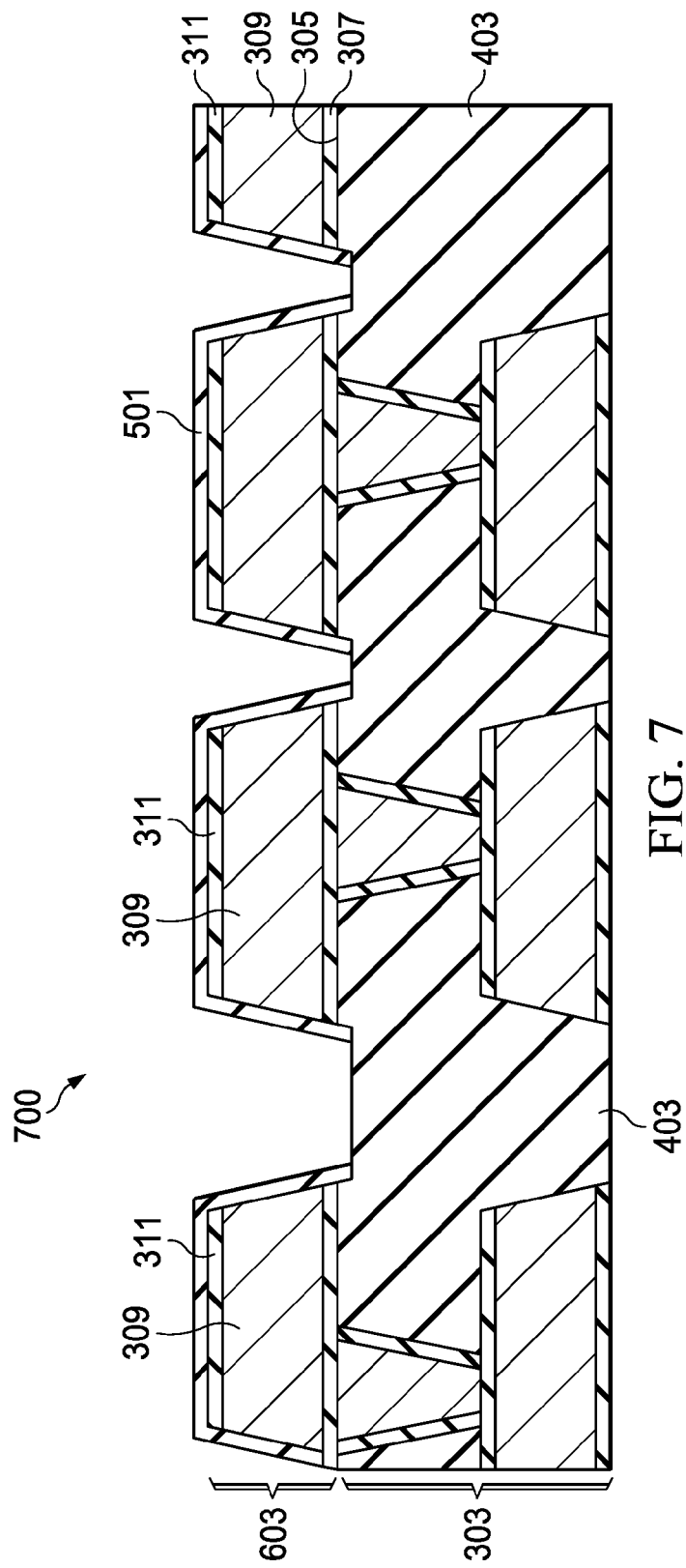

FIG. 7 is a cross sectional diagram of a work piece 700 including top metal stacks 603 over a metal layer 303 and IMD 403. Each of the top metal stacks include an underlayer 307, a top metal 309 over the underlayer 309, an ARL 311 over the top metal 309, and a protective layer 501 over the ARL 311 and peripherally surrounding the top metal 309 covering the sidewalls. After operation 263, the top metal stack is formed and the process refers back to FIG. 2A.

Figure 8:
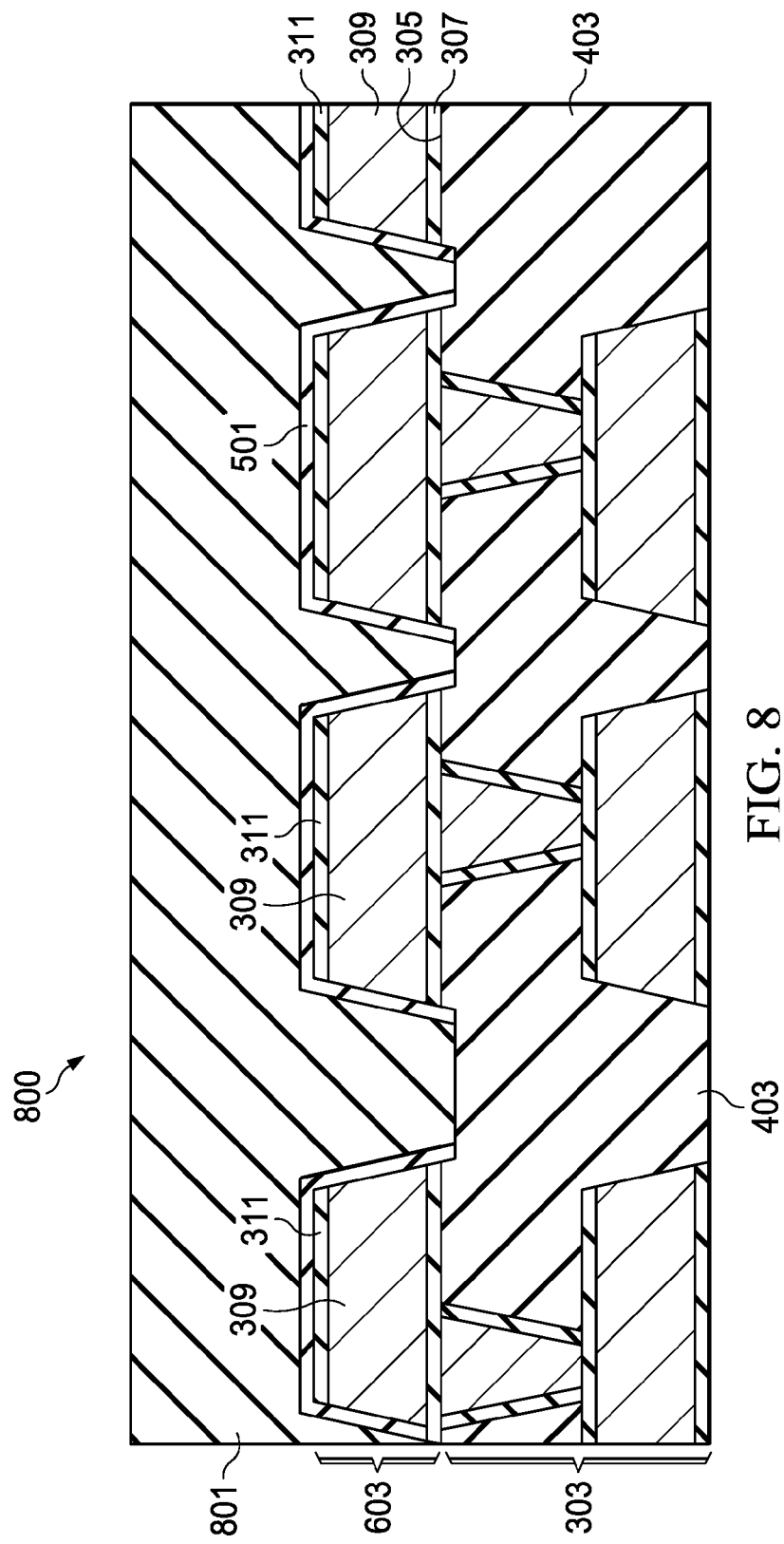

In operation 210 of FIG. 2A, a passivation layer is formed over the top metal stacks. The passivation layer is deposited over the top metal stack and between adjacent top metal stacks. The passivation layer is a dielectric material deposited using CVD processes and may be silicon oxide, silicon nitride, or other commonly used passivation material. FIG. 8 is a cross-sectional view of a portion of a workpiece 800 after operation 210 of FIG. 2A. The workpiece 800 includes a passivation layer 801 over a top metal stacks 603. The passivation layer fills the trench areas between the top metal stacks 603, including any openings in the IMD 403 removed when layers above are over etched.

Figure 9:
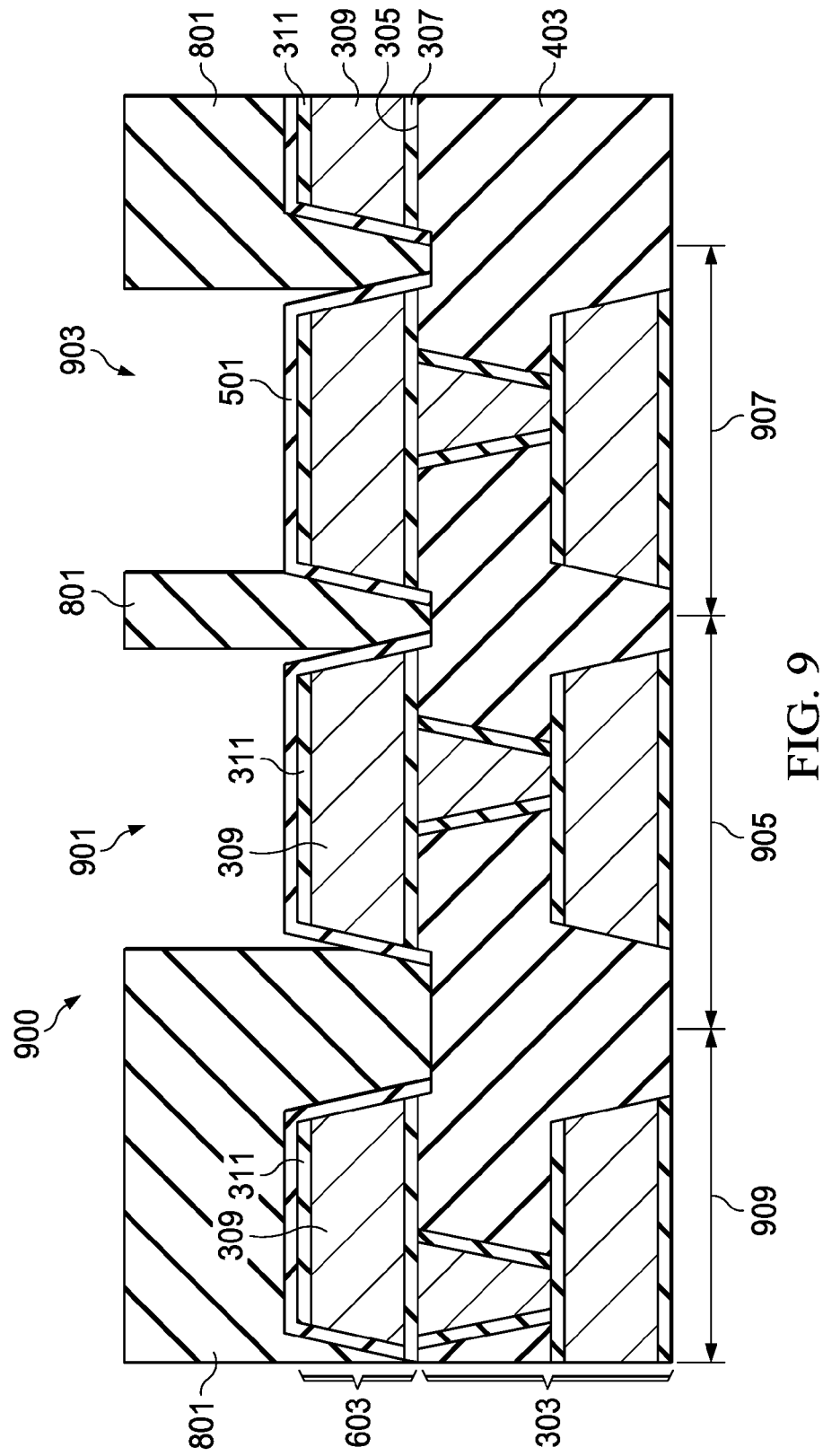

In operation 212 of FIG. 2A, microwells are etched in the passivation layer to expose some top metal stacks. A layer of photoresist is patterned to a width. The width may be about the same as a top width of the top metal stack or larger than the top width of the top metal stack. Using the patterned photoresist as an etch mask, openings are etched in the passivation layer to expose some metal plates. The etch process may be a wet etch or a dry etch. In a wet etch, an ethant is selected that stops at the protective layer. For example, M2 acid ($HNO_3$+ $CH_3COOH$+$H_3PO_4$) would stop a titanium nitride protective layer while etching the passivation layer material over the top metal stack. In a dry etch, a portion of the protective layer may be removed along with the passivation layer. FIG. 9 is a cross-sectional view of a portion of a workpiece 900 after operation 212. Openings 901 and 903 are etched in the passivation layer 801 to expose portions of the top metal stack 603, respectively. The workpiece 900 is separated into different regions 905, 907, and 909 to show different processing scenarios. Region 905 includes an opening 901 that is aligned with the top metal stack 603. A portion of the protective layer 501 on the top metal stack is shown to be removed during the etch process. Some passivation material 801 adjacent to the top metal stack 603 may also be removed during the etch process when the width being etched is larger than the top width of the top metal stack 603. Region 907 includes an opening 903 that is not perfectly aligned with the top metal stack 603. As result, the opening exposes some sidewall of the top metal stack 603 only on one side. Additional passivation material 801 is also removed from one side of the top metal stack 603. Depending on the etch selectivity and materials used for the passivation layer 801 and protective layer 501, in some embodiments, the protective layer 501 is not removed during the etch process, as shown in region 907. However, the dimensions of the opening is such that such misalignment does not cause the opening to expose adjacent top metal stacks. The top metal stack 603 in region 909 is not exposed by an opening. The top metal stack 603 in region 909 is not used as a floating gate of a BioFET.

Figure 10:
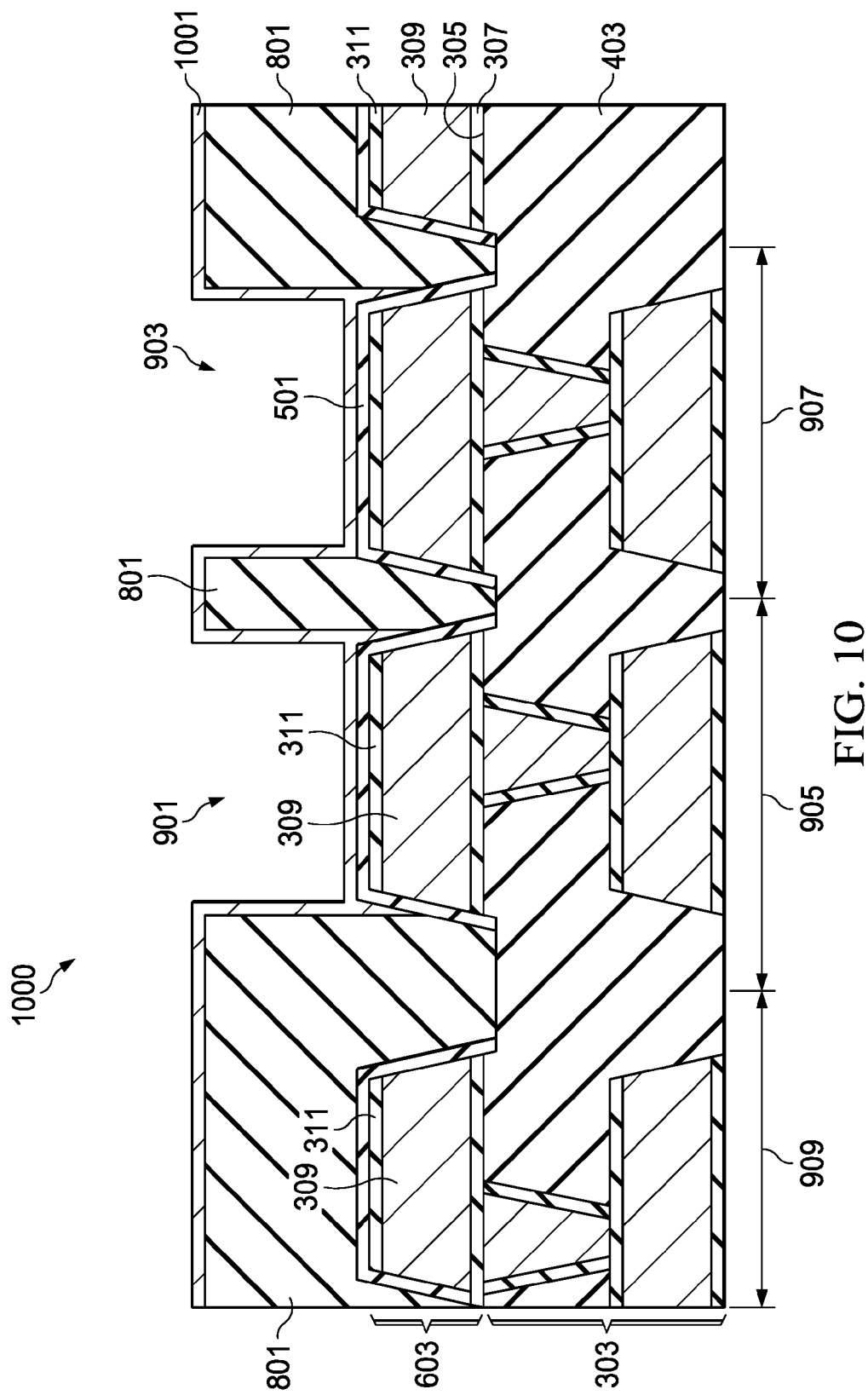

Referring back to FIG. 2A, in operation 214 a sensing layer is deposited in the microwells and over a field between the microwells. The sensing layer is deposited using spin-on coating, CVD or PVD processes having good coverage for the sidewalls of the microwells. In some embodiments, an atomic layer deposition (ALD) process is used to conformally coat the bottom and sidewalls of the microwells and the field between the microwells. The deposition process is selected so that even entrenched sidewall profiles can be conformally coated. The sensing layer may be titanium nitride, tungsten, a high-k dielectric such as aluminum oxide, lanthanum oxide, hafnium oxide, and tantalum oxide. The sensing layer is deposited to a sufficient thickness so that electrical signals representing conditions of the analyte in the microwells can be transmitted to the gate below. The sensing layer may bind directly to biomolecules in the test sample or indirectly through a surface treatment or bioreceptors. The sensing layer may further include self-assembled monolayers (SAM) and a support medium such as hydrogel. FIG. 10 is a cross-sectional view of a portion of workpiece 1000 after operation 214. A sensing layer 1001 is deposited over the wafer and in the microwells 901 and 903. Depending on the deposition process, the sensing layer may not have uniform thickness in the field portion between microwells and the sidewalls in the microwells. Complete sidewall coverage ensures that more binding sites are available on the sensing layer for the biomolecules.

Referring back to FIG. 2A, in operation 216 at least the field portion of the sensing layer is removed. Removing the field portion of the sensing layer isolates the sensing layer for different BioFETs from each other and prevents signal cross talk. Operation 216 includes a number of steps. A photoresist layer is deposited on the wafer and planarized. The photoresist is then patterned to form openings to expose the sensing layer on field areas between the microwells. The photoresist may be etched with an end point detection to ensure only the various photoresist layers are removed. Exposed sensing layer is removed from field areas depending on the material. For certain metal sensing layers, for example, titanium nitride, high-k dielectric material (aluminum oxide, lanthanum oxide, hafnium oxide, tantalum oxide, etc), a selective etch is performed to remove the sensing layer on the field areas without damaging microwell sidewalls. Then the remaining photoresist over the microwells is removed by ashing. In some embodiments, the photoresist for operation 216 has an opposite exposure from the photoresist for operation 212. Using the opposite exposure photoresist allows the same photomask to be used for both operations. For other sensing layers, for example, hydrogel, a selective chemical mechanical polishing (CMP) process is used without using a photoresist. The selective CMP removes the hydrogel in the field areas between the microwells without damaging the hydrogel in the microwells.

Figure 11:
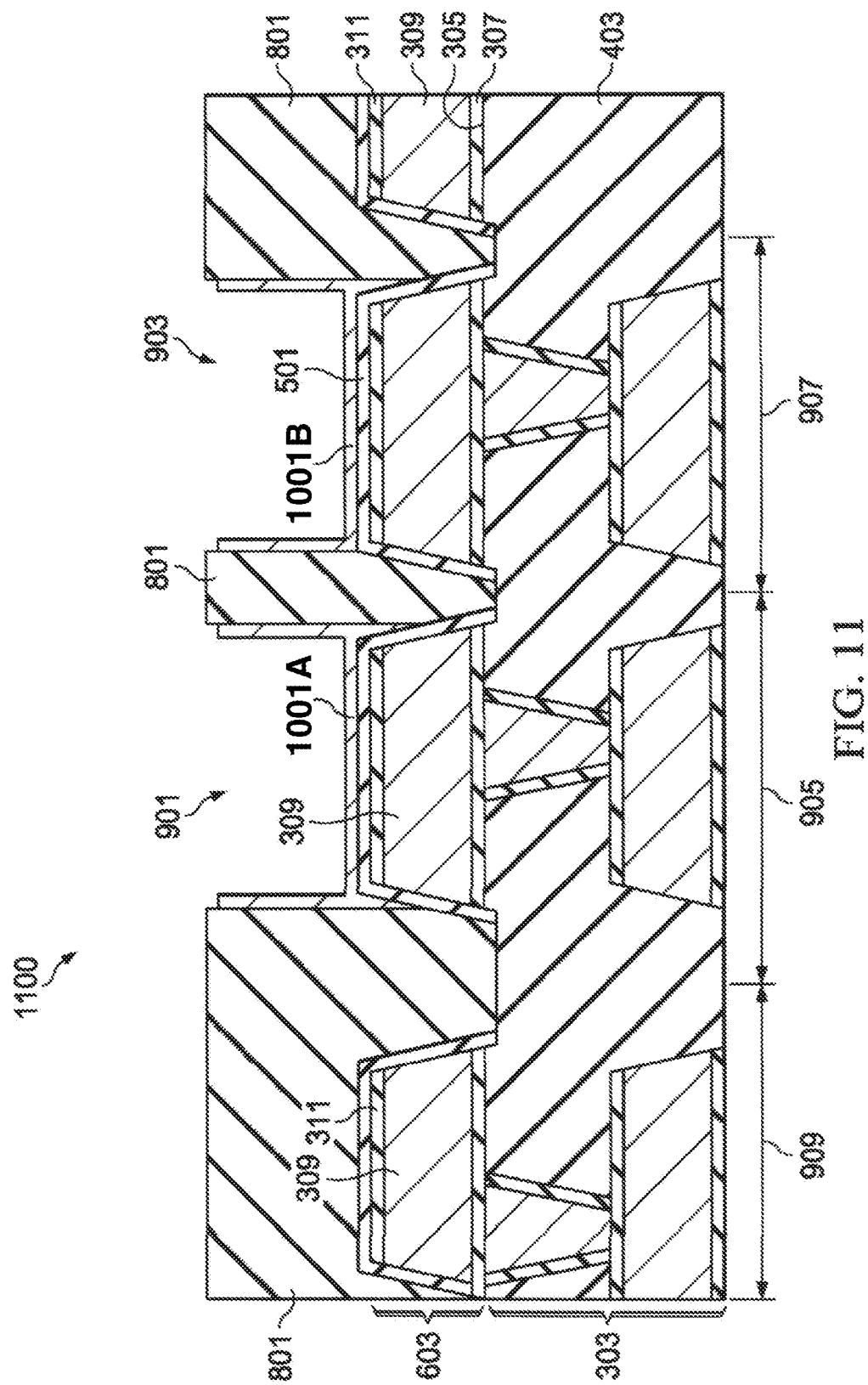

FIG. 11 is a cross-sectional view of a portion of workpiece 1100 after operation 216. Sensing layers 1001A and 1001B cover the sidewalls and bottoms of microwells 901 and 903, which are isolated from each other. When the photoresist is etched back, the corners of the microwells 901 and 903 are exposed, allowing a wet etchant to remove the sensing layer from upper portions of the microwell sidewalls. When a CMP process or a wet etch is used to remove the sensing layer from the field areas, some sensing layer from upper portions of the microwell sidewalls may also be removed. As shown, a small edge portion of the sensing layers 1001A and 1001B are removed from the lips of the microwells 901 and 903 by the selective metal etching process. In other embodiments, the sensing layers 1001A and 1001B completely covers the sidewalls of the microwells 901 and 903. The photoresist may completely cover the edges of the sidewalls during a dry etch to remove the sensing layer from the field areas. When a dry etch is used to remove the sensing layer from the field areas, the sidewalls of the microwells may remain completely covered by the sensing layer.

Referring back to FIG. 2, in optional operation 218, openings are formed to expose a second subset of the top metal stacks. The second subset of the top metal stacks is the bond pads used for externally connecting the BioFET device. The opening is formed by first depositing and patterning a photoresist layer over the wafer and etching through the pattern. In the same etch operation or a different etch operation, a protective layer and an antireflective layer is removed in the exposed portions of the second subset of the top metal stacks in operation 220. The etch operation may also remove a portion of the top metal in the top metal stack.

Figure 12:
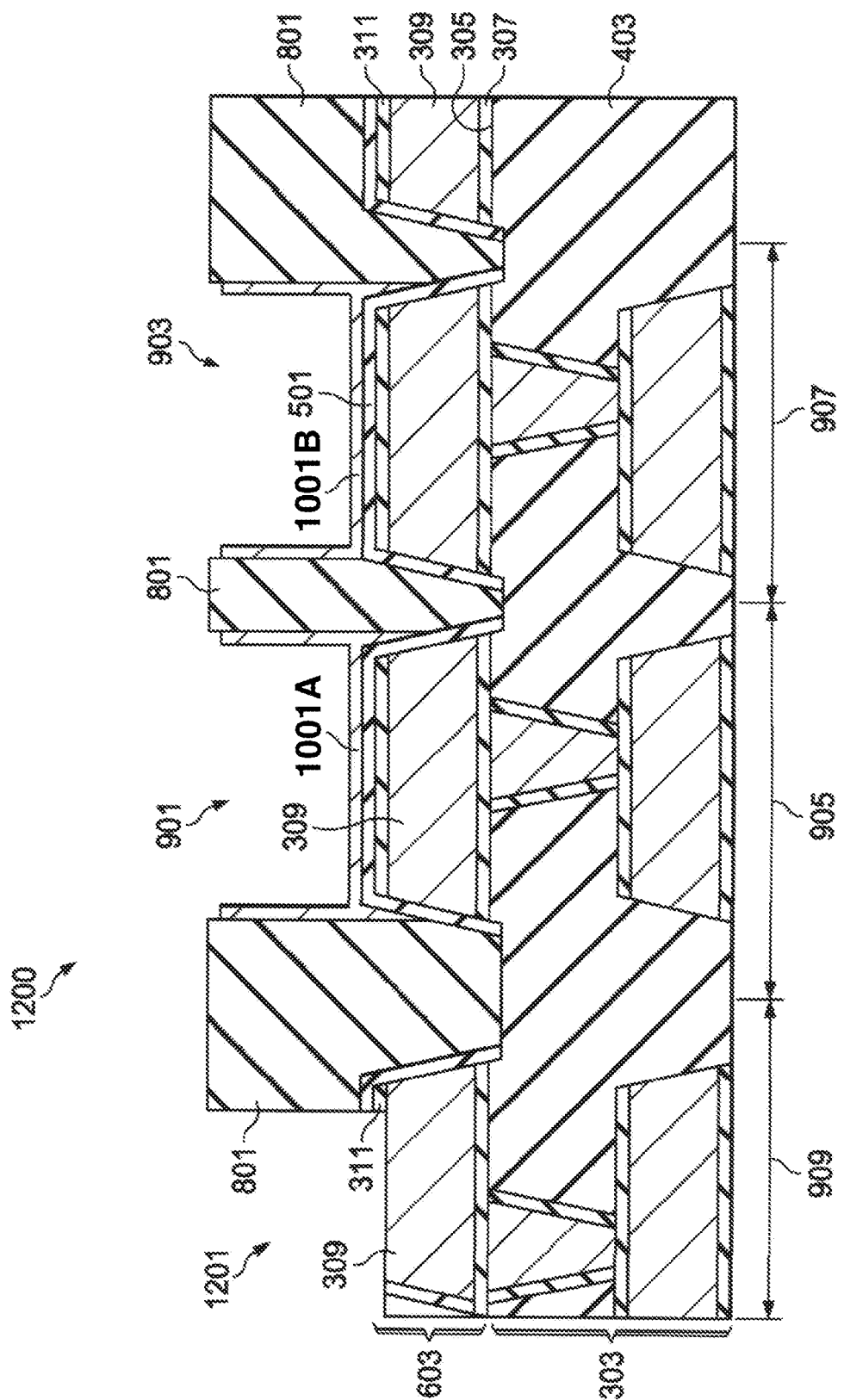

FIG. 12 is a cross-sectional view of a portion of workpiece 1200 after operation 218 and 220. Opening 1201 is formed in region 909 to expose top metal 309 as a bond pad. In some embodiments, the operations 216, 218 and 220 may be partially combined to reduce the number of processes. For example, photoresist material in the microwells 901 and 903 may be ashed with the photoresist material from operation 218 and 220.

Referring back to FIG. 2A, in operational operation 222, contacts may be formed between the top metal and the second subset of the top metal stacks and a package terminal. In some embodiments, wires are bonded to the bond pads to transmit power and signal. In other embodiments, conductive members such as bumps and pillars are used to externally connect the BioFET device.

In addition to the processes described in association with FIG. 2A, the sensing layer surface may be treated. The treatment may include depositing a chemical to render the surface hydrophilic or hydrophobic. In some cases, the treatment may modify the surface to have certain conductance or magnetic properties. The treatment may also include depositing a support medium for attaching receptors. For example, hydrogel or agar may be deposited to the sensing surface.

In some embodiments, BioFET device includes a microfluidic structure over the microwells. The microfluidic structures may include micropumps and valves and magnetic material or ferromagnetic material for magnetophoresis, metals for electrophoresis, electro wetting on dielectric (EWOD) or particular dielectric material for dielectrophoresis. The microfluidic structure may also electrically connect to the various bond pads adjacent to the microwells. The microfluidic structure has a bottom that seals the field area between adjacent microwells and provides channels for flowing reagents and test samples. The microfluidic structure may be transparent or partially transparent to allow observation of the reactions. In other embodiments, the microwells on the BioFET device is accessed from the top without a cover. Microfluidic channels may be formed directly in the passivation layer.

Figure 13:
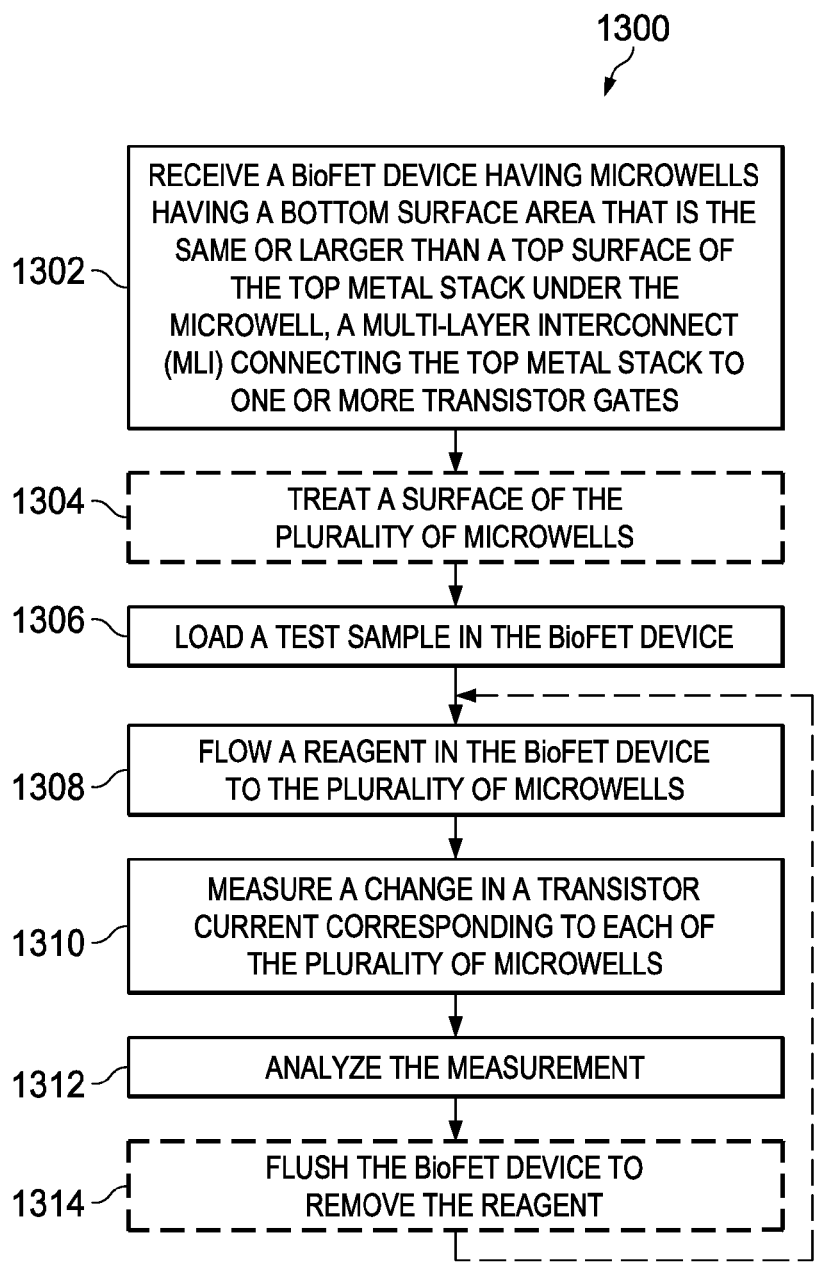
FIG. 13 is a flow chart of a method embodiment of using a BioFET device according to one or more aspects of the present disclosure.

FIG. 13 is a flow chart of an embodiment of a method 1300 of using a BioFET device according to one or more aspects of the present disclosure. In operation 1302, a BioFET device is received. The BioFET device is as described in various embodiments of the present disclosure. The BioFET device has a plurality of microwells, wherein a bottom surface area of the microwell is the same or larger than a top surface of the top metal stack under the microwell. The BioFET device also includes a multi-layer interconnect (MLI) connecting the top metal stack to one or more transistor gates. In optional operation 1304, a surface of the microwells is treated. In some embodiments, the BioFET device is received with the treatment already performed. In other embodiments, the treatment is performed before after receipt of the BioFET device. The treatment operation may include labeling, or functionalizing, the sensing layer with certain chemicals or biomolecules as receptors. The receptors may be enzyme, antibody, ligand, peptide, nucleotide, cell of an organ, organism or piece of tissue is provided or bound on the sensing layer for detection of a target biomolecule. For instance, to detect ssDNA (single-stranded deoxyribonucleic acid), the sensing film may be functionalized with immobilized complementary ssDNA strands. Also, to detect various proteins such as tumor markers, the sensing film may be functionalized with monoclonal antibodies. The receptors may be a part of self-assembled monolayer (SAM) of molecules. The SAM may have head groups of silane groups, silyl groups, silanol groups, phosphonate groups, amine groups, thiol groups, alkyl groups, alkene groups, alkyne groups, azido groups, or expoxy groups. The receptors are attached to the head groups of SAM.

In operation 1306 of method 1300, a test sample is loaded in the BioFET device. The test sample may be in a carrier medium. In some embodiments, the test sample is bound to a carrier bead. In other embodiments, the test sample is suspended in a fluidic medium. The loading operation flows the test sample to various microwells where they are bound directly or indirectly to the sensing layer.

In operation 1308, a reagent is flowed in the BioFET device to the microwells. The reagent reacts with some or all of the test samples in the microwells. The existence of reaction or the extent of the reaction is recorded by measuring the current through the source and drain of the BioFET in operation 1310. Several measurements of the current may be made at different times. For example, a blank measurement may be made to establish the baseline with deionized water. Another measurement may be made after the test sample is loaded to establish a second baseline. One or more measurements may be made to record the change in current during the reagent flow and residence in the BioFET device. In some embodiments, FET devices operate in linear region for detection. In some embodiments, FET device operate in saturation region for detection.

In operation 1312, the measurement is analyzed. The measurement may be outputted by the BioFET device to a computer or a processor to analyze the signals. In some embodiments, an analog signal is first converted to a digital signal. The data may be analyzed by a processor running a software program or by a user. In some embodiments, the measurement is analyzed on board the BioFET device.

The BioFET device may be a single use or a multiple use device. In optional operation 1314, the BioFET device is flushed to remove the reagent from the microwells and operations 1308 to 1312 repeated with a second reagent. The test sample remains in the BioFET device as different reagents are cycled through. This process may be used to identify an unknown substance. By recording reactions using different reagents, the identity of an unknown substance may be narrowed down. This process may be used to perform DNA sequencing. For example, a test sample of strands of DNA may be loaded into BioFET device. The strands may be amplified in each microwell to form a colony. By sequentially adding reagents containing different nucleobases and measuring reactions in each microwell, the identity of the strand in each microwell may be found.

In one aspect, the present disclosure pertains to a biological field-effect transistor (BioFET) device that includes a substrate and a number of BioFETs. The BioFET includes a microwell having a bottom and sidewalls, a number of top metal stacks under the microwells, each of the top metal stacks being under one microwell, and one or more transistors, wherein a gate of each of the one or more transistors is connected to one of the plurality of top metal stacks through intervening metal layers. The bottom is a sensing layer and at least a portion of the sidewalls is a sensing layer. Each top metal stacks include an underlayer, a top metal over the underlayer, and a protective layer over and surrounding the top metal; and the underlayer and the protective layers are conductive.

In another aspect, the present disclosure pertains to a method of forming a BioFET device. The method includes forming a number of FETs on a semiconductor substrate, forming a gate contact on the gate structure in each of the FETs, forming one or more metal interconnect layers over the FETs, forming a number of top metal stacks having a protective layer on sidewalls of a top metal, forming a passivation layer over the top metal stacks, etching microwells in the passivation layer to expose a subset of the top metal stacks, depositing a sensing layer in the microwells and over a field portion between the microwells, and removing at least the field portion of the sensing layer. The FETs each includes a gate structure formed on a first surface of the semiconductor substrate and a channel region. The bottom surface area of the microwells is larger than a top surface of the subset of the plurality of top metal stacks. The sensing layer fills any openings between the subset of the plurality of top metal stacks and the passivation layer.

An advantageous feature of illustrated embodiments may include a biological field-effect transistor (BioFET) device, comprising a substrate, and a plurality of BioFETs. Each BioFET comprises a plurality of microwells having a bottom and sidewalls, wherein the bottom is a sensing layer and at least a portion of the sidewalls is a sensing layer, and further comprises a plurality of top metal stacks under the plurality of microwells, each of the plurality of top metal stacks being under one microwell. Each of the plurality of the top metal stacks includes an underlayer, a top metal over the underlayer, and a protective layer over and surrounding the top metal and wherein the underlayer and the protective layers are conductive. Each BioFET further includes one or more transistors, wherein a gate of each of the one or more transistors is connected to one of the plurality of top metal stacks through intervening metal layers.

Another advantageous feature of illustrated embodiments may include a device, comprising a substrate and a BioFET structure. The BioFET structure includes a microwell having a bottom and sidewalls, wherein the bottom and at least a portion of the sidewalls form a sensing layer. A top metal stack is under the microwell, the top metal stack including a major conductive feature sandwiched between a conductive underlayer and a conductive protective layer, the conductive protective layer being conformal to a top surface of the major conductive feature. The device further includes a transistor, electrically connected to the major conductive feature through one or more intervening metal layers.

Yet another advantageous feature of illustrated embodiments may include a device comprising a transistor, and an interconnect structure electrically connected to the transistor. The interconnect structure includes a top metal stack that has a conductive underlayer, a conductive line atop the underlayer, and a conductive protective layer atop the conductive line and extending along sidewalls of the conductive line. The device further includes a passivation layer atop the top metal stack having a microwell formed therein, wherein sidewalls of the microwell are formed from the passivation layer and a bottom of the microwell is formed from the conductive protective layer. A sensing layer lines the bottom and at least partially lines the sidewalls of the microwell.

In yet another aspect, the present disclosure pertains to a method of sensing bio-reactions. The method includes receiving a BioFET device as disclosed in the present disclosure, loading a test sample in the BioFET device, flowing a reagent in the BioFET device to the plurality of microwells, measuring a change in a transistor current corresponding to each of the plurality of microwells, and analyzing the measurement.

In describing one or more of these embodiments, the present disclosure may offer several advantages over prior art devices. In the discussion of the advantages or benefits that follows it should be noted that these benefits and/or results may be present is some embodiments, but are not required in every embodiment. Further, it is understood that different embodiments disclosed herein offer different features and advantages, and that various changes, substitutions and alterations may be made without departing from the spirit and scope of the present disclosure.

What is claimed is:

1. A biological field-effect transistor (BioFET) device, comprising:
    a substrate; and
    a plurality of BioFETs, each BioFET comprising:
        a plurality of microwells having a bottom and sidewalls, wherein the bottom and at least a portion of the sidewalls is a sensing layer;
        a plurality of top metal stacks under the plurality of microwells, each of the plurality of top metal stacks being under one microwell, wherein each of the plurality of the top metal stacks includes an underlayer, a top metal over a top surface of the underlayer and not extending below the top surface of the underlayer, and a protective layer over and along a sidewall of the top metal, wherein a portion of the protective layer extends lower than an uppermost surface of the underlayer and wherein the underlayer and the protective layers are conductive; and
        one or more transistors, wherein a gate of each of the one or more transistors is connected to one of the plurality of top metal stacks through intervening metal layers.

2. The BioFET device of claim 1, further comprising a metal pad having a top surface below a plane of top surfaces of the plurality of top metal stacks.

3. The BioFET device of claim 1, wherein the each of the plurality of top metal stacks also includes an antireflective layer over the top metal and under the protective layer.

4. The BioFET device of claim 1, wherein a thickness of the protective layer on sidewalls of the top metal stacks is greater than 200 angstroms.

5. The BioFET device of claim 1, wherein a thickness of the protective layer on sidewalls of the top metal stacks is about 300 angstroms.

6. The BioFET device of claim 1, wherein the protective layer comprises titanium nitride.

7. The BioFET device of claim 1, further comprising:
    a fluidic channel fluidly connecting the microwells between the plurality of BioFETs.

8. The BioFET device of claim 1, wherein a bottom surface area of each of the plurality of microwells is larger than a top surface of the top metal.

9. The BioFET device of claim 1, wherein the sensing layer comprises a high-k dielectric.

10. The BioFET device of claim 1, wherein the sensing layer is disposed between a top portion of the plurality of top metal stacks and a passivation layer, wherein the passivation layer is disposed between each of the plurality of BioFETs.

11. The BioFET device of claim 10, wherein the sensing layer does not cover a top surface of the passivation layer.

12. A device, comprising:
    a substrate; and
    a BioFET structure including:
        a microwell having a bottom and sidewalls, wherein the bottom and at least a portion of the sidewalls form a sensing layer;
        a top metal stack under the microwell, wherein the top metal stack includes a major conductive feature sandwiched between a conductive underlayer and a conductive protective layer, the conductive protective layer being conformal to a top surface and one or more sidewalls of the major conductive feature and extending to an uppermost surface of the underlayer, the major conductive feature not extending below the uppermost surface of the underlayer; and
        a transistor, electrically connected to the major conductive feature through one or more intervening metal layers.

13. The device of claim 12, wherein the microwell is formed in a passivation layer formed over the top metal stack.

14. The device of claim 12, wherein the protective layer comprises titanium nitride.

15. The device of claim 12, further including an anti-reflective coating sandwiched between the major conductive feature and the conductive protective layer.

16. The device of claim 12, wherein the bottom of the microwell is substantially aligned with the major conductive feature.

17. A device comprising:
    a transistor;
    a interconnect structure electrically connected to the transistor, the interconnect structure including a top metal stack comprising: a conductive underlayer, a conductive line atop the underlayer and not along sides of the underlayer, and a conductive protective layer atop the conductive line and extending along sidewalls of the conductive line;
    a passivation layer atop the top metal stack having a microwell formed therein, wherein sidewalls of the microwell are formed from the passivation layer and a bottom of the microwell is formed from the conductive protective layer; and
    a sensing layer lining the bottom and at least partially lining the sidewalls of the microwell, wherein an uppermost surface of the passivation layer extends above the sensing layer.

18. The device of claim 17, wherein the conductive protective layer comprises titanium nitride.

19. The device of claim 17, wherein the interconnect structure includes a plurality of conductive elements vertically stacked atop one another and electrically interconnected by conductive vias.

20. The device of claim 17, wherein the top metal stack is vertically aligned to the transistor.

21. The device of claim 17, wherein the sensing layer extends from a top to a bottom of the sidewalls.

22. The device of claim 17, wherein a portion of the protective layer extends lower than an uppermost surface of the underlayer.

* * * * *